United States Patent [19]

Beyer, Jr.

[11] Patent Number: 5,801,177

[45] Date of Patent: Sep. 1, 1998

[54] METHOD FOR CONTROLLING AND/OR LOWERING SERUM GLUCOSE AND FATTY ACID CONCENTRATIONS AND HYPERTENSIVE BLOOD PRESSURE IN NON-INSULIN-DEPENDENT DIABETIC PATIENTS

[76] Inventor: Karl H. Beyer, Jr., 1001 Gypsy Hill Rd., Penllyn, Pa. 19422

[21] Appl. No.: 572,743

[22] Filed: Dec. 14, 1995

[51] Int. Cl.$^6$ ................................................. A61K 31/495
[52] U.S. Cl. ................................................. 514/255; 514/866
[58] Field of Search ................................................. 514/255

[56] References Cited

U.S. PATENT DOCUMENTS

| | | |
|---|---|---|
| 3,313,813 | 4/1967 | Cragoe . |
| 4,594,349 | 6/1986 | Beyer, Jr. . |
| 4,663,322 | 5/1987 | Beyer, Jr. . |
| 4,920,123 | 4/1990 | Beyer, Jr. . |
| 4,952,582 | 8/1990 | Beyer, Jr. . |
| 5,110,817 | 5/1992 | Beyer, Jr. . |
| 5,130,333 | 7/1992 | Bergman et al. ................. 514/295 |

OTHER PUBLICATIONS

Chemical Abstracts AN 1990:42594, Onada et al, 1990.

J. Clin Pharmacol, 1996, vol. 52, pp. 135–144, "Studies on Pyrazinoylguanidine, 1. Characterization of Metabolic Effects in Diabetic Rats", Jousif I. A–Rahim.

J. Clin Pharmacol, 1996, vol. 52, pp. 145–152, "Studies on Pyrazinoylguanidine, 2. Comparative Drug and Dose Effects on Glucose and Lipid metabolism in Streptozotocin–Induced Diabetic Rats", Jousif I. A–Rahim.

M Mosby Year Book, 1992, pp. 3–20, "Management of Diabetes Mellitus, Perspectives of Care Accros the Life Span", Robert E. Ratner.

J. Clin Pharmacol, 1994, vol. 34, pp 1234–1245, "Pyrazinoylguanidine Downregulates the Glucose Fatty–Acid Cycle in Hypertensive, Hyperinsulinemic Diabetic Patients", Elliot S. Vesell et al.; Jan. 13, 1995.

J. Clin Pharmacol, 1993, vol. 33, pp. 823–831, "Effects of Pyrazinoylguanidine on the Glucose–Fatty Acid Cycle in Normal Subjects and Patients with Non–Insulin–Dependent Diabetes Mellitus", Elliot S. Vesell et al; Sep. 27, 1993.

"Studies on Pyrazinoylguanidine", Yousif I. A–Rahim et al, pp. 1–16; In Press, 1993.

M Mosby Year Book, pp. 3–20, "Management of Diabetes Mellitus, Perspectives of Care Across the Life Span", Robert E. Ratner, 1992.

Diabetes, 1992, vol. 41, pp. 123–129, Perspectives in Diabetes, HLA and Insulin–Dependent Diabetes, Protective Perspective, Michael J. Sheehy.

The FASEB Journal, Aug. 1993, vol. 7, pp. 1092–1096, "Autoimmune Diabetes Results from Genetic Defects Manifest by Antigen Presenting Cells", David V. Serreze.

J. Clin. Invest, Mar. 1985, vol. 75, pp. 809–817, "Hyperinsulinemia", Michaela Modan et al.

Diabetics Care, Apr. 1993, vol. 16, No. 4, pp. 642–652, "Undiagnosed NIDDM: Clinical and Public Health Issues", Maureen I. Harris, Ph.D.

The American Journal of Medicine, Jan. 1981, vol. 70, pp. 142–150, "Insulin Action", Michael P. Czech, Ph.D.

Diabetes, Dec. 1976, vol. 25, No. 12, pp. 1154–1162, "The Insulin Receptor: Its Role in Insulin Resistance of Obesity and Diabetes", Jerrold M. Olefsky, M.D.

The Lancet, Apr. 13, 1963, pp. 728–789, "The Glucose Fatty–Acid Cycle".

J. Clin. Invest, Nov. 1983, vol. 72, pp. 1737–1747, "Effect of Fatty Acids on Glucose Production and Utilization in Man", Eleuterio Ferrannini et al.

Hypertension, Apr. 1991, vol. 17, No. 4, pp. 565–573, "Obesity, Glucose Intolerance, Hyperinsulinemia, and Response to Antihypertensive Drugs" Michaela Modan et al.

AJH, Apr. 1993, vol. 6, No. 4 (Supplement), pp. 123–134, "Ionis Basis of Hypertension, Insulin Resistance, Vascular Disease, and Related Disorders, the Mechanism of Syndrom X," Lawrence M. Resnick.

Journal of Clinical Endocrinology and Metabolism, 1981, vol. 53, No. 6, pp. 1256–1262, "Differential Effects of Tolbutamide on First and Second Phase Insulin Secretion in Noninsulin–Dependent Diabetes Mellitus", Michael A. Pfeifer et al.

The Journal of Biological Chemistry, 1987, vol. 262, No. 6, pp 2608–2612, "Increased Cytosolic Calcium, a Signal for Sulfonylurea–Stimulated Insulin Release from Beta Cells", T. Yap Nelson et al.

(List continued on next page.)

Primary Examiner—Keith D. MacMillan
Attorney, Agent, or Firm—Oblon, Spivak, McClelland, Maier & Neustadt, P.C.

[57] ABSTRACT

The present invention is a method of treating non-insulin-dependent diabetes mellitus comprising administering to a patient in need thereof a therapeutically effective amount of at least one compound of formula (I) for a period of time of more than 6 days:

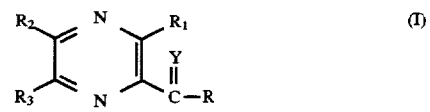

wherein

Y is O

R is OH, NHCONR$^4$R$^5$, or N=C(NR$^4$R$^5$)$_2$;

R$^4$ and R$^5$ are each independently selected from the group consisting of hydrogen; C$_{1-10}$ alkyl, straight or branched chain; aryl C$_{1-14}$ alkyl; and mono- or disubstituted aryl C$_{1-4}$ alkyl where the substituents are fluoro, chloro, bromo, iodo or C$_{1-10}$ alkyl, straight or branched chain; R$^1$ and R$^2$ are each independent selected from the group consisting of hydrogen, amino, and mono- or di-substituted amino where the substituents are C$_{1-10}$ alkyl, straight or branched chain C$_{3-8}$, cycloalkyl; provided that R$^1$ and R$^2$ may not both be amino or substituted amino; and R$^3$ is hydrogen, trifluoromethyl; fluoro; chloro; bromo; or iodo; or a pharmaceutically acceptable salt thereof.

11 Claims, 3 Drawing Sheets

OTHER PUBLICATIONS

*Diabetes*, Sep. 1984, vol. 33, pp. 838–845, "Mechanism of Improvement in Glucose Metabolism After Chronic Glyburide Therapy" Donald C. Simonson et al.

*Diabetes*, Feb. 1981, vol. 30, pp. 148–162, Lilly Lecture 1980 "Insulin Resistance and Insulin Action, an In Vitro and In Vivo Perspective" Jerrold M. Olefsky.

*Drugs & Aging*, 1994, vol. 4, No. 6, pp. 470–490, "Treatment of Non–Insulin–Dependent Diabetes Mellitus and Its Complications, a State of the Art Review", Aldo Ilarde et al.

*The Lancet*, Mar. 13, 1996, "Deterioration of Glucose Tolerance in Hypertensive Patients on Prolonged Diureic Treatment", P. J. Lewis et al.

*The American Journal of Medicine*, Nov. 1984, vol. 77, pp. 823–827, "Elevated Hemoglobin $A_{1c}$ and Low–Density Lipoprotein Cholesterol Levels in Thiazide–Treated Diabetic Patients", Zachary T. Bloomgarden et al.

*British Medical Journal*, Jan. 20, 1979, pp. 159–161, "Beta–Adrenoceptor–Blocking Drugs and Blood Sugar Control in Diabetes Mellitus", A.D. Wright et al.

*Acta Med Scand Suppl.*, 1983, vol. 672, pp. 69–77, "β–Adrenergic Blockade and Diabetes Mellitus", Jan Ostman.

*Journal of Hypertension*, 1989, vol. 7, pp. 551–559, "Metabolic Effects of Diltiazem and Atenolol: Results from a Randomized, Double–Blind Study with Parallel Groups", Thomas Pollare et al.

*Diabetes*, Jun. 1975, vol. 24, No. 6, pp. 547–551, "Calcium Antagonists and Islet Function", G. Devis et al.

*The New England Journal of Medicine*, Sep. 28, 1989, vol. 321, No. 13, pp. 868–873, "A Comparison of the Effects of Hydrochlorothiazide and Captopril on Glucose and Lipid Metabolism in Patients with Hypertension" Thomas Pollare et al.

*Scand J. Clin. Lab Invest.*, 1974, vol. 34, pp. 312–315, "Hypotensive Therapy Reduces Microvascular Albumin Leakage in Insulin–Dependent Diabetic Patients with Nephropathy", H.–H. Parving et al.

*The Lancet*, Nov. 19, 1994, vol. 344, pp. 1383–1389, "Randomised Trial of Cholesterol Lowering in 4444 Patients with Coronary Heart Disease: The Scandinavian Simvastatin Survival Study (4S)", Scandinavian Simvastatin Survival Study Group.

*Acta. Med. Scand*; 1962, vol. 172, pp. 641–645, "The Effect of Nicotinic Acid on the Plasma Free Fatty Acids".

*Metabolism*, Feb. 1994, vol. 13, No. 2, pp. 181–189, "The Effect of Nicotinic Acid in Diabetes Mellitus", George D. Molnar et al.

*Physician's Desk Reference*, 1994 (Supplements for Revision), pp. 1496–1498.

*Pharmacology*, 1992, vol. 44, pp. 124–138, "Inhibition of Urea Transport Across Renal Tubules by Pyrazinoylguanidine and Analogs", Karl H. Beyer, Jr. et al.

*J. Clin. Pharmacol*; 1992, vol. 32, pp. 1128–1134, "Pyrazinoylguanidine: Antihypertensive, Hypercholesterolemic, and Renin Effects", Charles E. Chambers et al.

*J. Clin. Pharmacol.*, 1993, vol. 33, pp. 554–561, "Contrasting Effects of Pyrazinoylguanidine and Hydrochlorothiazide in Patients with Renal Insufficiency", Karl. H. Beyer et al.

*Diabetologia*, 1987, vol. 30, pp. 622–626, "Insulin Suppression of Plasma–Free Fatty Acid Concentration in Normal Individuals and Patients with Type 2 (Non–Insulin–Dependent) Diabetes", A.L.M. Swislocki et al.

*Pharmacological Basis of Therapeutics*, 1990, 8th Edition, pp. 727–728, Goodman and Gilman.

*Annu. Rev. Med.*, 1993, vol. 44, pp. 121–131, "Role of Insulin Resistance in Human Disease (Syndrome X): An Expanded Definition", Gerald M. Reaven, M.D.

*JAMA*, Dec. 11, 1967, vol. 202, No. 11, pp. 116–122, "Effects of Treatment on Morbidity in Hypertension", Veterans Administration Cooperative Study Group of Antihypertensive Agents.

*American Heart Journal*, Aug. 1986, vol. 112, No. 2, pp. 432–437, "The Triglyceride Issue: A View From Framingham", William P. Castelli.

*JAMA*, 1984, vol. 251, No. 3, pp. 365–374, "The Lipid Research Clinics Coronary Primary Prevention Trial Results, II. The Relationship of Reduction in Incidence of Coronary Heart Disease to Cholesterol Lowering", Lipid Research Clinics Program.

*Pharmacology*, 1996, vol. 52, pp. 135–144, "Studies on Pyrazinoylguanidine, 1. Characterization of Metabolic Effects in Diabetic Rats", Jousif I. A–Rahim.

*Pharmacology*, 1996, vol. 52, pp. 145–152, "Studies on Pyrazinoylguanidine, 2. Comparative Drug and Dose Effects on Glucose and Lipid Metabolism in Streptozotocin–Induced Diabetic Rats", Jousif I. A–Rahim.

*M. Mosby Year Book*, 1992, pp. 3–20, "Management of Diabetes Mellitus, Perspectives of Care Across the Life Span", Robert E. Ratner.

FIG. 2

METHOD FOR CONTROLLING AND/OR LOWERING SERUM GLUCOSE AND FATTY ACID CONCENTRATIONS AND HYPERTENSIVE BLOOD PRESSURE IN NON-INSULIN-DEPENDENT DIABETIC PATIENTS

BACKGROUND OF THE INVENTION

1. Field of the Invention

This invention relates to a method of controlling serum glucose, fatty acid concentration, blood pressure, and in general relieving some of the symptoms of non-insulin dependent diabetic patients.

2. Discussion of the Background

Diabetes mellitus has been defined as "a clinical syndrome characterized by a relative or inadequate deficiency of insulin or by a resistance to the action of insulin."[1] The definition is appropriate to the forms of diabetes that can be identified (1) as insulin dependent diabetes mellitus (IDDM), or Type I, that requires injections of insulin to manage their loss of or insufficient pancreatic β-cell production of insulin. Prior to the availability of insulin for injection, these were called juvenile diabetics because of their early onset of the, then, fatal disease. These have come to be recognized as of genetic origin, an autoimmune disease.[2,3]

(2) Non-insulin dependent diabetes mellitus patients (NIDDM), or Type II, frequently have an increase[4] or partial deficiency of insulin production, depending on how long the NIDDM has persisted. Their insulin response to hyperglycemia is insufficient for its purpose. Because a first purpose of insulin is to facilitate adequate glucose uptake for metabolism by tissues such as skeletal and cardiac muscle, these patients are said to be resistant to available insulin. Of the 13 to 15 million diabetic patients in the USA, it is estimated that up to 90% are NIDDM. By the use of surveys designed to represent their distribution, half of these NIDDM patients are undiagnosed, hence untreated.[5] Insulin production may or may not be adequate for glycemic control by proper diet and/or drug therapy.

Two determinants that influence importantly insulin resistance of cell membrane to glucose entry are: (1) availability of insulin receptors at the cell membrane, the number and activation of which is insulin-dependent,[6,7] and (2) the plasma level of free fatty acids (FFA) from foodstuff and/or the lipolysis of triglyceride stores, principally in adipose tissue. Lipolysis induced by hormones, such as Norepinephrine, increases FFA blood levels available especially to muscle[8] as a sustaining source of energy. As the blood level of FFA increases, resistance of the cell membrane to glucose uptake (insulin resistance) increases.[7-9] Conversely, increased insulin blood levels as induced by the endogenous generation of hyperglycemia or by a high glucose meal (a glucose tolerance test for example)[10] can inhibit lipolysis, and thus reduce serum FFA levels and its impedance of glucose uptake by the cells. In the non-diabetic, active person this shifting balance of a normal range of glycemia, insulin blood level and FFA lipemia makes possible exertion, sustained physical effort and consciousness over a period of hours or days between meals.

The NIDDM person is less capable of sustaining this dietary shifting balance of glycemia, insulin and FFA levels. Some may be able to approximate a normal metabolic balance if a proper diet of carbohydrate, fat and protein intake is adhered to. Exercise, a balanced life style and adjustment to or relief from stress contribute together with diet as basic therapy for these patients. Weight reduction may be an important feature of this behavior pattern since overweight and hypertension are common characteristics of NIDDM diabetes.[11,12]

If this regimen of diet, exercise and adjustment to stress is insufficient to control blood sugar within appropriate limits, a sulfonylurea drug may suffice to lower blood glucose levels toward normal. These drugs are reported to stimulate insulin release from pancreatic β-cells[13,14] and to increased insulin sensitivity at cell surfaces.[15,16] They are usually taken just before a meal or meals. The initial (primary) response to sulfonylureas may be inadequate in 25 to 30% of patients. With time another 5 to 10% of patients develop resistance to these drugs.[17]

Sulfonylureas are not antihypertensive agents nor do they lower hyperlipidemic blood levels. Thus, ancillary antihypertensive and antihyperlipidemic therapy are required to diminish the high risk of cardiovascular insults such as atherosclerosis and coronary heart disease—the most frequent cause of death of these patients.

Such generally employed antihypertensive agents as thiazides[18,19] and β-adrenergic blocking[20,21] drugs adversely effect glucose and lipid metabolism in NIDDM persons. Most, but not all, calcium channel blocking drugs are less offensive in this regard.[22,23] Angiotensin converting enzyme inhibitors do not reduce either hyperglycemia or hyperlipidemia. Their antihypertensive effect is their supportive role for these diabetic patients.[24,25] Hydroxymethylglutaryl-coenzyme-A reduction inhibitors of cholesterol synthesis are relatively ineffective in lowering the frequent hyperlipidemia derived from triglyceride synthesis or lipolysis.[26]

Nicotinic acid inhibits triglyceride hydrolysis to FFA and glycerol[27] but is reported to be contraindicated for diabetics.[28] Amiloride, a 2,4,5-tri-polar substituted pyrazinoic acid derivative is commonly employed in formulation with a thiazide (hydrochlorothiazide) so that its potassium-retaining characteristic will offset the kaliuresis induced by the thiazide. However, amiloride or its thiazide combination should be avoided for diabetic patients because of the possibility of inducing hyperkalemia. The combination should be avoided, also, for at least 3 days before glucose tolerance testing.[29]

There is accordingly a need for a compound that can safely address these several needs of NIDDM patients for reduction and control of hyperglycemia, of insulin, of free fatty acid and triglyceride blood levels, and of essential (adrenergic) hypertension.

SUMMARY OF THE INVENTION

Accordingly, it is an object of this invention to provide a method for lowering and/or controlling the blood sugar levels of NIDDM persons.

Another, correlative, object of this invention is to provide a method for lowering and/or controlling the FFA and triglyceride blood levels of NIDDM persons.

These and other objects, which will become apparent from the description of the invention given herein below, have been discovered by the inventor to be all satisfied by administering to a patient in need thereof of an effective amount of at least one compound of the formula (I), wherein:

Y is O, R is OH, NHCONR$^4$R$^5$; or N=C(NR$^4$R$^5$)$_2$, where R$^4$ and R$^5$ are each independently selected from the group consisting of hydrogen; C$_{1-10}$ alkyl, straight or branched chain; aryl C$_{1-4}$ alkyl; mono or disubstituted aryl C$_{1-4}$ alkyl where the substituents are fluoro, chloro, bromo, iodo, trifluoromethyl, or C$_{1-10}$, alkyl, straight or branched chain;

R$^1$ and R$^2$ are each independently selected from the group consisting of hydrogen, amino and mono or disubstituted amino where the substituents are C$_{1-10}$ alkyl, straight or branched chain, or C$_{3-8}$ cycloalkyl; provided that R$^1$ and R$^2$ may not both be amino or substituted amino; and R$^3$ is hydrogen; trifluoromethyl; fluoro; chloro; bromo; or iodo; or a pharmaceutically acceptable salt thereof.

Aryl typically refers to 6 member aromatic rings, and may include other aromatic ring systems.

BRIEF DESCRIPTION OF THE FIGURES

A more complete appreciation of the invention and many attendant advantages will be readily obtained as the same become better understood by reference to the following detailed description when considered in connection with the accompanying drawings.

DETAILED DESCRIPTION OF THE PREFERRED EMBODIMENTS

While studying pyrazinoylguanidines and their 3-amino analogs as inhibitors of urea and salt reabsorption by the kidney (i.e., as hyperuretic and saluretic agents)[30], the inventor discovered that in addition to lowering urea blood levels and decreasing hypertensive blood pressure[31] these compounds and in particular the representative pyrazinoylguanidine (PZG) decreased serum concentration of triglycerides and cholesterol.[32] Furthermore, whereas PZG had no effect on normal glucose serum concentrations, it was capable of blocking the increased serum glucose and insulin concentrations normally induced by hydrochlorothiazide in the oral glucose tolerance test (GTT).[33]

A significance of the present discovery is that when administered to NIDDM patients as initial, replacement or adjunctive therapy, compounds of formula (I), and pyrazinoylguanidine by example, are capable of lowering plasma hyperglycemia, insulin, FFA, triglycerides and cholesterol of the fasting NIDDM patient whose only therapy prior to PZG was his diet, Table 1. This effect of PZG in lowering the hyperglycemia, hypertriglyceridemia and free fatty acid plasma levels has been confirmed in streptozotocinized diabetic rats, Table 2.

Alternatively, when PZG was added as a supplement to the ongoing hyperglycemic, hyperlipidemic and antihypertensive therapy of NIDDM patients without regard for kind or dosage, PZG was capable of lowering and/or controlling blood hyperglycemia, FFA, triglyceridemia and hypertensive blood pressure, Table 3.

TABLE 1

PYRAZINOYLGUANIDINE (PZG) REDUCED FASTING GLUCOSE, LIPIDS, INSULIN, C-PEPTIDE, AND GLUCAGON PLASMA (OR SERUM) LEVELS OF DIET CONTROLLED NON-INSULIN-DEPENDENT DIABETIC PATIENT (JD) WHO RECEIVED NO OTHER THERAPY

| PHASE OR %± | GLU MG/DL | INS µIU/ML | C-PEP NG/ML | GLUC PG/ML | FFA MG/DL | TG MG/DL | HDL MG/DL | CHOL MG/DL |
|---|---|---|---|---|---|---|---|---|
| PLACEBO | 172 | 18 | 3.5 | 142 | .43 | 200 | 38 | 235 |
| PZG | 149 | 13 | 2.7 | 130 | .21 | 169 | 40 | 220 |
| %± | −13 | −28 | −23 | −8 | −51 | −16 | +5 | −6 |

% CHANGE = INCREASE (+) OR DECREASE (−). PZG VALUES 600 MG BID, PO, 3-WEEK ADMINISTRATION COMPARED TO PLACEBO CAPSULES OF IDENTICAL APPEARANCE. SINGLE-BLIND STUDY, NO OTHER THERAPY.

TABLE 2

PYRAZINOYLGUANIDINE (PZG) REDUCED SERUM GLUCOSE, TRIGLYCERIDES, FREE FATTY ACIDS AND CHOLESTEROL VALUES COMPARED TO PLACEBO EFFECT IN FASTING FEMALE ADULT STREPTOZOTOCINIZED (STZ) RATS HANDLED IN RANDOM SEQUENCE.[34]

| (N = 8 RATS IN EACH GROUP) | GLUCOSE MG/DL | TRIGLYCER-IDES MG/DL | FFA MG/DL | CHOLES-TEROL MG/DL |
|---|---|---|---|---|
| NORMAL VALUES,[1] CONTROL, NO DRUG | 122 ± 28 | 84 ± 21 | .64 ± .1 | 49 ± 12 |
| STZ, NO THERAPY[2] | 471 ± 71 | 621.7 ± 213 | 1.1 ± .3 | 65 ± 5 |

TABLE 2-continued

PYRAZINOYLGUANIDINE (PZG) REDUCED SERUM GLUCOSE, TRIGLYCERIDES, FREE FATTY ACIDS AND CHOLESTEROL VALUES COMPARED TO PLACEBO EFFECT IN FASTING FEMALE ADULT STREPTOZOTOCINIZED (STZ) RATS HANDLED IN RANDOM SEQUENCE.[3,4]

| (N = 8 RATS IN EACH GROUP) | GLUCOSE MG/DL | TRIGLYCER-IDES MG/DL | FFA MG/DL | CHOLES-TEROL MG/DL |
|---|---|---|---|---|
| STZ, PLACEBO Rx[3] | 455 ± 83 | 699 ± 289 | .63 ± .1 | 62 ± 7 |
| STZ, PZG Rx[4] | 306 ± 22* | 231 ± 40* | .52 ± .04 | 55 ± 7[NS] |

[1]PLASMA VALUES, X̄ ± SD 8 NORMAL RATS FROM SAME GROUP AS OTHERS INJECTED WITH STZ WITH OR WITHOUT DRUGS.
[2]STZ = STREPTOZOTOCIN 50 MG/KG IN 50 Mm CITRATE I.P. SINGLE INJECTION 7 DAYS PRIOR TO BLOOD WITHDRAWN FOR ANALYSIS.
[3]PLACEBO Rx = N SALINE I.P., BID; BLOOD FOR ANALYSES 14 DAYS AFTER STZ INJECTION, 7 DAYS OF PLACEBO INJECTIONS.
[4]PZG 50 MG/KG IN N SALINE I.P., BID; BLOOD FOR ANALYSIS 14 DAYS AFTER STZ INJECTION, 7 DAYS OF PZG INJECTIONS.
* = P < .001 PZG COMPARED TO PLACEBO DATA
NS = NOT SIGNIFICANT, P > .05 tance to PZG was apparent. This result was not discovered in the 6 day or less trial, as no steady state could be reached in such a short period of time.

Figure 1:
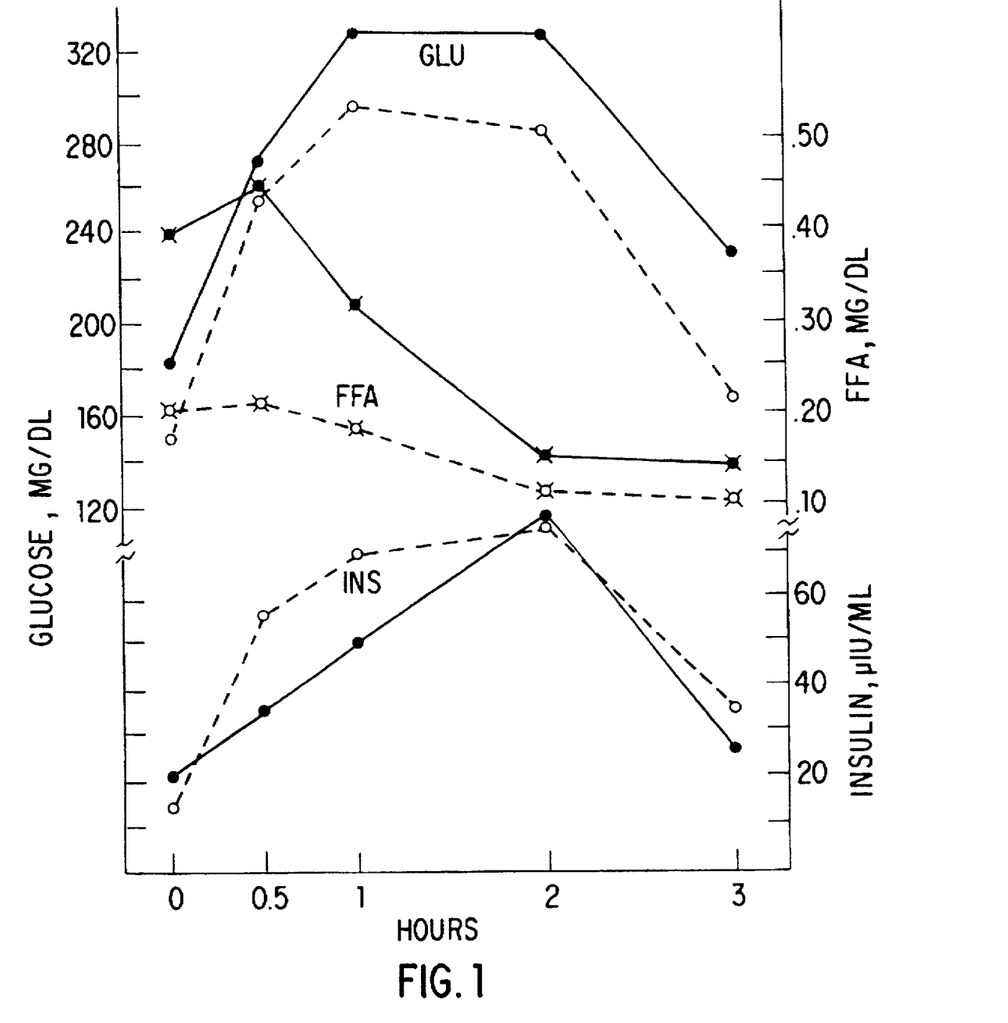
FIG. 1 Oral glucose tolerance response of patient JD (diet therapy) for glucose (GLU), free fatty acids (FFA) and insulin (INS) during placebo control phase (●—● or ■—■) and after 3 weeks during pyrazinoylguanidine 600 mg bid po drug therapy (○—○ or □—□). Drawn from data in Vesell et al., courtesy of J. Clin. Pharmacol. 34:1234–1245, 1994.
Figure 1A:
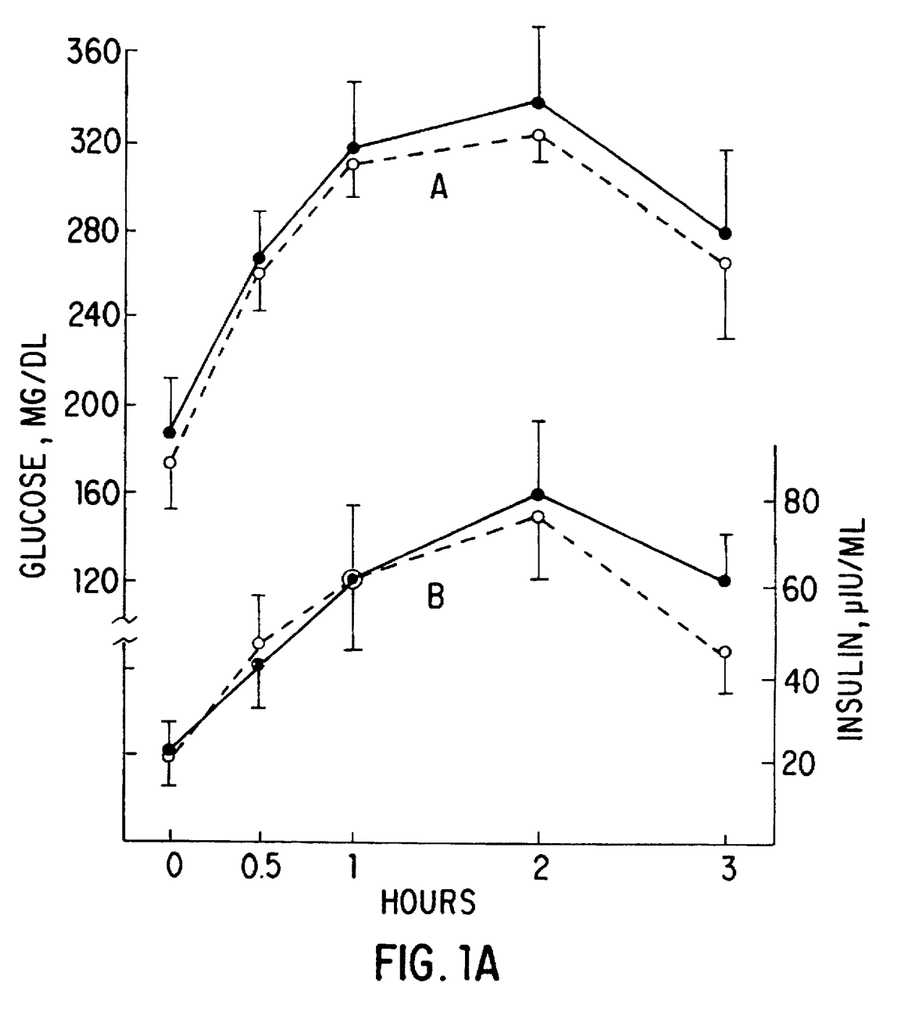
FIG. 1A Oral glucose tolerance curves showing in 8 patients with NIDDM mean and standard error for glucose (A) and insulin (B), during placebo control phase (●—●) and after 3 weeks during pyrazinoylguanidine 600 mg bid po drug therapy (○—○). Drawn from Vesell et al., J. Clin. Pharmacol. 34:1234–1245, 1994.

The mean glucose tolerance test values for glucose and insulin of eight patients were plotted (FIG. 1A). The trend of the data was toward the more marked differences observed in a single patient (FIG. 1), who received no drug therapy. The reduced mean effect for the eight patients arises from several sources, in particular large interpatient variations in response to the different continuing therapies on which PZG was superimposed.

Most preferred compounds of the invention are those wherein for the compound of Formula (1), Y is O, one of $R^1$ and $R^2$ is hydrogen; and $R^3$ is hydrogen. Particularly preferred compounds of Formula (I) are the following: pyrazinoylguanidine and 3-aminopyrazinoylguanidine.

As should be noted by the structure of the preferred compounds of the present invention, the present compounds are distinguished from amiloride by the fact that those of this invention possess a low level of substitution. Amiloride is characterized by having two amino substituents, one chloro substituent and one-CONHC(=NH)NH$_2$ substituent. The

TABLE 3

SUPPLEMENTARY EFFECT OF PYRAZINOYLGUANIDINE (PZG) (600 MG, P.O., B.I.D.) VS PLACEBO ADDED TO ONGOING SULFONYLUREA HYPERGLYCEMIA THERAPY (6 OF 8 PATIENTS), CALCIUM CHANNEL OR β-BLOCKER ANTIHYPERTENSIVE THERAPY (6 OF 8 PATIENTS) AND A 3-HYDROXYMETHYLGLUTARYL COENZYME-A REDUCTASE INHIBITOR FOR ONE PATIENT.[10]

| N = 8 | GLUCOSE MG/DL | FFA MG/DL | TRI-GLYCERIDES MG/DL | T-CHOLESTEROL MG/DL | BLOOD PRESSURE SYS/DIAS. MMHG |
|---|---|---|---|---|---|
| X̄ ± SD PLACEBO PHASE | 186 ± 65 | .52 ± .18 | 226 ± 141 | 183 ± 28 | 150 ± 14/86 ± 5 |
| X̄ ± SD PZG PHASE | 174 ± 63 | .40 ± .18 | 215 ± 152 | 179 ± 25 | 132 ± 18/65 ± 6 |

Moreover, fully effective doses of PZG may be added to or discontinued as supplement to other NIDDM therapy promptly without inducing untoward hypoglycemia, hyperglycemia or aberrant changes in measured lipids or blood pressure.

Furthermore, the inventor has discovered that compounds of formula (I), and PZG by example, when used for an extended period of time stimulates especially the first phase of insulin response to hyperglycemia, FIG. 1. In doing so PZG lowers serum FFA levels promptly and activates glucose uptake as by the direct effect of insulin at the cell membrane receptors and by reducing the effect of the (lowered) FFA serum level on glucose uptake.

Figure 2:
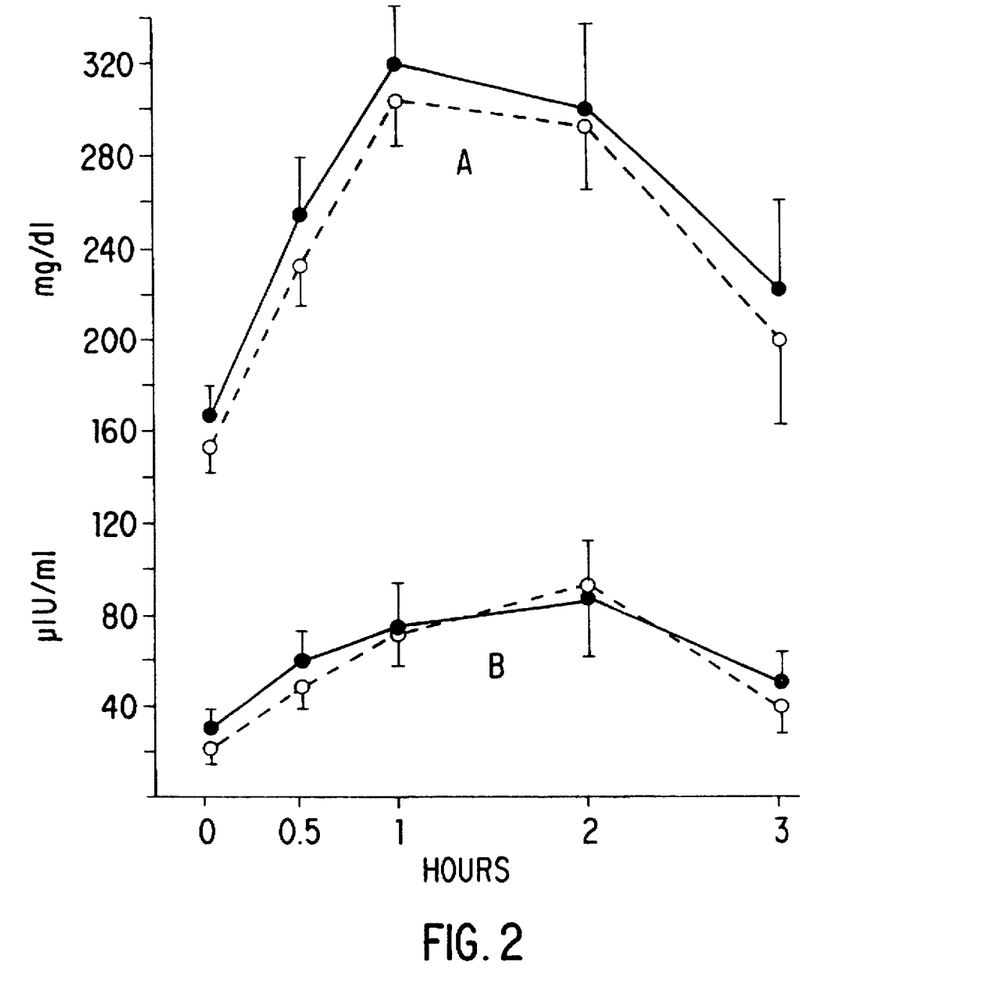
FIG. 2: Non-insulin-dependent diabetic control, placebo, glucose tolerance curve (—●—) and during pyrazinyoylg-nanidine (PZG) administration for 6 days (—○—). B: Corresponding plasma insulin curves. 8 diabetic patients, SEM.

The increase of insulin in the first phase of insulin response to hyperglycemia under extended therapy is especially surprising. In extended therapy of a patient only on diet therapy for 3 weeks, this initial effect is quite prominent, with insulin levels more than 30% higher, as compared to the control phase, FIG. 1. Previous studies gave no indication that the plasma insulin levels would be improved in this fashion. No increase in plasma insulin over the controls was observed with a collection of NIDDM patients, allowed to maintain their normal therapies, when the treatment was conducted for only a short time (6 days or less), FIG. 2.

Patients do not build up resistance to the compounds of Formula (I). Unlike sulfonylureas, no development of resismultipolar amiloride-like compounds, including its 5-fluoro analog for example, share a potassium retaining hyperkalemic characteristic[36] that has precluded general use of amiloride except in formulations to counteract the kaliuretic effect of other drugs, such as thiazides. The preferred examples of this invention are devoid of excessive retention or excretion of potassium.

It should be recognized that since these are pharmaceutical compounds it is conceivable that one of the metabolites of these compounds may be directly responsible in whole or in part for the lowering or control of glycemia, lipidemia or hypertension discovered by the inventor.

The formula (I) compounds can be used in the form of salts derived from inorganic or organic acids. Included among such salts are the following: adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, toxylate, and undecanoate.

Combinations of the present invention may be administered orally, parenterally or rectally in dosage unit formulations containing conventional non-toxic pharmaceutically acceptable carriers, adjuvants and vehicles. The term parenteral as used herein includes subcutaneous injection, intravenous or intramuscular injection or infusion techniques. The invention is effective in the treatment of non-insulin-dependent diabetes mellitus, in the treatment of prediabetic hypertensive patients, and in the treatment of patients whose elevated glycemia, hyperlipidemia and hypertension combine as Syndrome X, risk factors for micro- or macro-cardiovascular lesions conducive to peripheral vascular and coronary artery disease.[12,38]

Pharmaceutical compositions containing the active ingredient may be in a form suitable for oral use, for example, as tablets, granules, hard or soft capsules prepared according to methods known to the art for the manufacture of pharmaceutical compositions, and such compositions may contain flavoring, coloring and/or preserving agents to convey a pharmaceutically elegant and palatable preparation.

The tablets and granules may be uncoated or coated by known methods to delay disintegration and absorption in whole or in part and to delay or prolong a sustained action over a longer period of time.

Dispensable powders and granules suitable for preparation of an aqueous suspension for immediate oral consumption provide the active ingredient admixed with a dispersing or wetting agent, a suspending agent and one or more preservatives, coloring and/or flavoring agents.

Sterile formulations for injectable solution may be prepared for packaging in dry filled form with non-toxic dispersing and solubilizing agents suitable for rapid solubilization in an aqueous solution such as normal saline for immediate injection subcutaneously, intramuscularly or intravenously.

Formulations of this invention may be administered in the form of suppositories for rectal administration prepared by mixing the drug in a suitable non-irritating non-hydrous excipient which is solid at ordinary temperature but which will melt and remain fluid at rectal temperature, such as cocoa butter or polyethylene glycols.

For the compounds of formula (I) dose levels of the magnitude of 50 to 2400 mg, preferably 300 to 1200 mg, especially 300 to 600/mg, including all values therebetween, per day are suitably, administered once or as fractional doses twice or three times per day (e.g., prior to meals) are therapeutically effective. The compounds may be used alone, or in conjunction with other therapies. Therapy is administered for more than 6 days, preferably for 3 weeks or more. Therapy may be continued until the end of the patients life.

A variety of other therapies may be administered simultaneously with the compounds of formula (I). Examples of these other therapies include diet therapy, as well as drugs such as Lovastatin, Glyburide, Tolbutamide, Glipizide, Verapamil, Diltiazem, Propranolol, Atenolol, Nadolol, Captopril, Enalapril and Chlorpropamide. The administration of these treatments is well known[17].

The compounds of formula (I) utilized in this invention are active on oral as well as parenteral administration.

The pyrazinoic acid derivatives utilized in the present invention may be prepared in accordance with well known procedures,[36] for example, those described in U.S. Pat. No. 3,313,813.

Whereas the singular features of compounds of formula (I) that relate to reduction of urea blood levels of azotemic patients, reduction of hypertensive blood pressure and hyperlipidemia have been described in my previous patents[39] and in our more general publications referred to herein, this invention brings to bear on a single clinical entity all these features of a single compound of formula (I) that contribute to the reduction and control of hyperglycemia and which may actually anticipate clinical NIDDM by several years[5] as recognized on the basis of family history and clinical chemistry as pre-NIDDM patients. Genetic screening for NIDDM allows for even more precise identification of these pre-NIDDM patents. Thus, in addition to its use and safety for the control of, or as supplement to, the therapy of NIDDM, a single compound such as a preferred embodiment of examples of formula (I) can be used as preventive therapy of NIDDM, as well as its more common side effects and mortality as represented by studies of antihypertensive,[40] antihypertriglyceridemic[41] and antihypercholesterolemic[42] therapy.

Obviously, numerous modifications and variations of the present invention are possible in light of the above teachings. It is therefore to be understood that within the scope of the appended claims, the invention may be practiced otherwise than as specifically described herein.

CITATIONS

1. Ratner R E: Management of Diabetes Mellitus: Perspectives of Care Across the Lifespan. 1992, Mosby.
2. Sheehy M J: HLA and insulin dependent diabetes. A protective perspective. Diabetes 1992;41:123–129.
3. Serreze D V: Autoimmune diabetes results from genetic defects manifest by antigen presenting cells. FASEB J. 1993;7:1092–1096.
4. Modan M, Halkin H, Almog S, Lusky A, Eshkol A, Shefi M, Shitrit A, Fuchs Z: Hyperinsulinemia: A link between hypertension, obesity and glucose intolerance. J. Clin. Invest. 1985;75:809–817.
5. Harris M I: Undiagnosed NIDDM: Clinical and Public Health Issues. Diabetes Care 1993;16:642–652.
6. Czech M P: Insulin action. Am. J. Med. 1981;70:142–150.
7. Olefsky J M: The insulin receptor: Its role in insulin resistance in obesity and diabetes. Diabetes 1976;25:1154–1162.
8. Randle P J, Hales C N, Garland P B, Newsholme E A: The glucose fatty acid cycle, its role in insulin sensitivity and the metabolic disturbances of diabetes mellitus. Lancet 1963; Apr. 13:785–789.
9. Ferrannini E, Barrett E J, Bevilacqua S, DeFronzo R A: Effect of fatty acids on glucose production and utilization in man. J. Clin. Invest. 1983;72:1737–1747.
10. Vesell E S, Chambers C E, Seaton T D, Passananti G T, Demers L M, Beyer K H: Pyrazinoylguanidine down regulates the glucose fatty-acid cycle in hypertensive, hyperinsulinemic diabetic patients. J. Clin. Pharmacol. 1994;34:1234–1245.
11. Modan M, Almog S, Fuchs Z, Chetrit A, Lusky A, Halkin H: Obesity, glucose intolerance, hyperinsulinemia and response to antihypertensive drugs. Hypertension 1991;17:565–573.
12. Resnick L M: Ionic basis of hypertension, insulin resistance, vascular disease and related disorders. The mechanism of "Syndrome X." Am. J. Hypertension 1993;6:123S–134S.
13. Pfeifer M A, Halter J B, Beard J C and Porte D: Differential effects of tolbutamide on first and second phase insulin secretion in noninsulindependent diabetes mellitus. J. Clin. Endocrinol. Metab. 1981;53:1256–1262.
14. Nelson T Y, Gaines K L, Rajan A S, Berg M, Boyd A E: Increased cytosolic calcium: A signal for sulfonylurea- 15. Simonson D C, Ferrannini E, Bevilacqua S, Smith D, Barrett E, Carlson R, DeFronzo R A: Mechanism of improvement in glucose metabolism after chronic glyburide therapy. Diabetes 1984;33:838–845.
16. Olefsky J M: Insulin resistance and insulin action: An in-vitro and in-vivo perspective. Diabetes 1981;30:148–162.
17. Ilarde A, Tuck M: Treatment of non-insulin-dependent diabetes mellitus and its combinations. Drugs-Aging 1994;4:470–491.
18. Lewis P J, Kohner E M, Petrie A, Dollery C T: Deterioration of glucose tolerance in hypertensive patients on prolonged diuretic treatment. Lancet 1976;1:564–566.
19. Bloomgarden Z T, Ginsberg-Fellner F, Rayfield E J, Bookman J, Brown W V: Elevated hemoglobin A1, and low-density lipoprotein cholesterol levels in thiazide-treated diabetic patients. Am. J. Med. 1984;77:823–827.
20. Wright A D, Barber S G, Kendall M J, Poole P H: β-Adrenoreceptor-blocking drugs and blood sugar control in diabetes mellitus. Brit. Med.J. 1979;1:159–161.
21. Ostman J: B-Adrenergic blockade and diabetes mellitus. Acta. Med. Scand. 1983;672 Suppl.:69–77.
22. Pollare T, Lithell H, Morlin C, Prantare H, Hvarfner A, Ljunghall S: Metabolic effects of diltiazem and atenolol: Results from a randomized, double-blind study with parallel groups. J. Hypertension 1989;7:551–559.
23. Devis G, Somers G, Van Obberghen E and Malaisse W J: Calcium antagonists and islet function: 1. Inhibition of insulin release by verapamil. Diabetes 1975;24:547–551.
24. Pollare T, Lithell H, Berne C: A comparison of the effects of hydrochlorothiazide and captopril on glucose and lipid metabolism in patients with hypertension. N. Engl. J. Med. 1989;321:868–873.
25. Parving H H, Smidt U M: Hypotensive therapy reduces microvascular albumin leakage in insulin-dependent diabetic patients with nephropathy. Diabet-Med. 1986;3:312–315.
26. Scandinavian Simvastatin Survival Study Group: Randomized trial of cholesterol lowering in 4444 patients with coronary heart disease. Lancet 1994;344:1383–1389.
27. Carlson L A and Oro L: The effect of nicotinic acid on the plasma free fatty acids. Demonstration of a metabolic type of sympathicolysis. Acta. Med. Scand. 1962;172:641–645.
28. Molnar G D, Berge K G, Rosevear J W, McGuckin W F, Achor R W P: The effect of nicotinic acid in diabetes mellitus. Metabolism 1964;13;181–190.
29. Physicians' Desk Reference. Moduretic. 48th Edition, pp. 1496–1498, 1994, Medical Economics Data Production Co., Montvale, N.J. 076451742.
30. Beyer K H, Gelarden R T, Vesell E S: Inhibition of urea transport across renal tubules by pyrazinoylguanidine and analogs. Pharmacology 1992;44:124–138.
31. Chambers C E, Vesell E S, Heim C, Passananti G T, Beyer K H: Pyrazinoylguanidine: Antihypertensive, hypocholesterolemic and renin effects. J. Clin. Pharmacol. 1992;32:1128–1134.
32. Beyer K H, Ward T D, Vary J E, Gelarden R T, Knutson D W, Vesell E S: Contrasting effects of pyrazinoylguanidine and hydrochlorothiazide in patients with renal insufficiency. J. Clin. Pharmacol. 1993;33:554–561.
33. Vesell E S, Chambers C E, Passananti G T, Demers L M, Beyer K H: Effects of pyrazinoylguanidine on the glucose-fatty acid cycle in normal subjects and patients with non-insulin-dependent diabetes mellitus. J. Clin. Pharmacol. 1993;33:823–831.
34. A Rahim Y I, Beyer, K H, Vesell E S: Studies of Pyrazinoylguanidine: 1. Characterization of Metabolic Effects in Diabetic Rats. Pharmacology. In Press.
35. Swislocki A L M, Chen J D I, Golay A, Chang M O, Reaven G M: Insulin suppression of plasma-free fatty acid concentration in normal individuals and patients with Type 2 (non-insulin-dependent) diabetes. Diabetologia 1987;30:622–626.
36. Cragoe E J: (3-Amino-,5,6-disubstituted-pyrazinoyl) guanidines. U.S. Pat. No. 3,313,813, Apr. 11, 1967.
37. Goodman and Gilman. The Pharmacological Basis of Therapeutics. 8th Edition, pp. 727–728, 1990, Pergamon Press, Inc., Elmsford, N.Y. 10523, USA.
38. Reaven G M: Role of insulin resistance in human disease (Syndrome X): An expanded definition. Annu. Rev. Med. 1993;44:121–131.
39. Beyer K H: U.S. Pat. Nos. 4,594,349; 4,663,322; 4,920, 123; 4,952,582; 5,110,817.
40. Veterans Administration Cooperative Study Group on Antihypertensive Agents: Effects of treatment on morbidity in hypertension. Results in patients with diastolic blood pressures averaging 115 through 129 mmHg. JAMA 1967;202:116–122.
41. Castelli W P: The triglyceride issue: A view from Framingham. Am. Heart J. 1986;112:432–437.
42. Lipid Research Clinics Program. The lipid research clinics coronary primary prevention trial results. 11. The relationship of reduction in incidence of coronary heart disease to cholesterol lowering. JAMA 1984;251:365–374.

What is claimed as new and is desired to be secured by Letters Patent of the United States is:

1. A method of treating non-insulin-dependent diabetes mellitus comprising administering to a patient in need thereof a therapeutically effective amount of at least one compound of formula (I) for a period of time of more than 6 days:

wherein

Y is O

R NHCONR$^4$R$^5$, or N=C(NR$^4$R$^5$)$_2$;

R$^4$ and R$^5$ are each independently selected from the group consisting of hydrogen; C$_{1-10}$ alkyl, straight or branched chain; aryl C$_{1-4}$ alkyl; and mono- or disubstituted aryl C$_{1-4}$ alkyl where the substituents are fluoro, chloro, bromo, iodo or C$_{1-10}$ alkyl, straight or branched chain;

R$^1$ and R$^2$ are each independent selected from the group consisting of hydrogen, amino, and mono- or di-substituted amino where the substituents are C$_{1-10}$ alkyl, straight or branched chain C$_{3-8}$, cycloalkyl; provided that R$^1$ and R$^2$ may not both be amino or substituted amino; and R$^3$ is hydrogen, trifluoromethyl; fluoro; chloro; bromo; or iodo; or a pharmaceutically acceptable salt thereof.

2. The method of claim 1, wherein R is N=C(NR$^4$R$^5$)$_2$.

3. The method of claim 1, wherein said compound is pyrazinoylguanidine.

4. The method of claim 1, wherein said compound is 3-aminopyrazinoylguanidine.

5. The method of claim 1, wherein said period of time is at least 3 weeks.

6. The method of claim 1, further comprising simultaniously administering a different drug therapy for treatment for NIDDM or the symptoms of NIDDM.

7. The method of claim 1, wherein said patient is not receiving any other drug therapy for the treatment of NIDDM.

8. The method of claim 1, wherein said therapeutically effective amount is 50 to 2400 mg per day.

9. The method of claim 1, wherein said therapeutically effective amount is 50 to 1200 mg per day.

10. The method of claim 1, wherein said therapeutically effective amount is 300 to 600 mg per day.

11. The method of claim 1, wherein said at least one compound is administered at least twice per day, orally.

* * * * *